US006175022B1

(12) United States Patent
Brungardt et al.

(10) Patent No.: US 6,175,022 B1
(45) Date of Patent: Jan. 16, 2001

(54) ALCOHOL-TERMINATED KETENE MULTIMER SIZING AGENTS

(75) Inventors: Clement L. Brungardt, Chester County, PA (US); Richard J. Riehle, New Castle County, DE (US); Ian Vallance, High Wycombe Bucks (GB); Jian Jian Zhang, New Castle County, DE (US)

(73) Assignee: Hercules Incorporated, Wilmington, DE (US)

( * ) Notice: Under 35 U.S.C. 154(b), the term of this patent shall be extended for 0 days.

(21) Appl. No.: 09/224,839

(22) Filed: Dec. 30, 1998

(51) Int. Cl.[7] .............................. C07D 305/14; B31B 1/02
(52) U.S. Cl. ............................ 549/510; 549/511; 428/84; 493/186
(58) Field of Search .................................. 549/510, 511; 428/84; 493/186

(56) References Cited

U.S. PATENT DOCUMENTS

| | | | | |
|---|---|---|---|---|
| 4,317,756 | * | 3/1982 | Dumas | 524/607 |
| 5,685,815 | * | 11/1997 | Bottorff et al. | 493/186 |
| 5,846,663 | * | 12/1998 | Brungardt et al. | 428/537.5 |

* cited by examiner

*Primary Examiner*—Ba K. Trinh
(74) *Attorney, Agent, or Firm*—Gary A. Samuels

(57) ABSTRACT

Nucelophilic group, such as alcohol, terminated 2-oxetanone multimers, process of making same by reacting e.g. alcohol and dicarboxylic acid chloride in the presence of triethylamine, and their use for sizing paper.

78 Claims, No Drawings

ALCOHOL-TERMINATED KETENE MULTIMER SIZING AGENTS

FIELD OF THE INVENTION

This invention relates to ketene multimer sizing agents and more particularly it relates to nucleophilic group terminated ketene multimer sizing agents.

BACKGROUND OF THE INVENTION

Sizing agents are added to fine paper to improve the runnability of the paper machine and improve the performance of the paper in end-use applications. Alkyl ketene dimer (AKD, e.g., Aquapel®364 dimer available from Hercules), alkenyl ketene dimer (AlkKD, e.g., Precis® 787 dimer available from Hercules), and alkenyl succinic anhydride (ASA) are the most commonly used internal sizing agents for paper made under alkaline conditions. Traditional AKD's are made by the dimerization of two saturated, straight-chain fatty acid chlorides (e.g., palmitic or stearic acid chlorides). Liquid AlkKDs can be made by dimerization of unsaturated or branched fatty acids (e.g., oleic or isostearic acid). ASA-based sizing agents are made by the reaction of maleic anhydride with an internal olefin (typically $C_{14}$–$C_{18}$). All three types of sizing agents—AKD, AlkKD, and ASA—have a reactive functional group that covalently bonds to cellulose pulp, and a hydrophobic tail that is oriented away from the pulp once the reaction has taken place. The nature and orientation of the hydrophobic tails causes the paper to repel water.

Although AKD, AlkKD, and ASA are all commercially successful, each has its shortcomings. Poor emulsion stability and deposits on the paper machine are the two most commonly cited shortcomings of ASA. ASA cannot be shipped and stored in emulsion form for long periods of time. The papermaker must make the ASA emulsion in the paper mill immediately before use. More importantly, even moderate addition levels of ASA can cause deposits on the paper machine, web breaks, and holes in the paper. ASA addition levels above 1.0–1.25 kg/metric tonne of paper general lead to unacceptable paper machine runnability and paper quality problems. Addition levels greater than 1.0–1.25 kg/metric tonne are often required to meet end-use sizing requirements, or to size paper grades made with high levels of filler.

Rate of sizing development is the most frequently cited shortcoming of AKD-based sizing agents. An extended period of curing is often required before sizing development is complete. In most cases, AKD sizing is completed by the time the paper has reached the winder. AKD-based sizing agents have also been associated with alkaline paper handling problems in high speed converting applications. Typical problems encountered with alkaline fine paper include: reduced operating speed, double feeds or jams in high speed copiers, paper welding, and registration errors on envelope folding and high speed printing equipment.

Commercial evaluations have consistently shown that liquid AlkKD's give sized paper with better handling performance than paper sized with traditional AKD's. Unfortunately, the improved paper handling performance generally comes at the expense of reduced sizing efficiency. Pilot scale testing has shown that none of the three commonly used reactive sizes—AKD, AlkKD, or ASA—can be used in size press applications without paper handling problems.

Polymeric surface sizing agents, such as Scripset 740 styrene maleic anhydride copolymer or Chromoset 600 styrene acrylate ester (available from Hercules Incorporated) have several advantages over reactive sizing agents added at the wet end. Adding the sizing agent at the size press develops sizing at the surface of the sheet where it is needed to obtain good black and white ink jet print quality, or resist the penetration of fountain solution on an offset press. Due to their high molecular weight, polymeric sizing agents generally do not cause the paper handling problems on high speed converting equipment or high speed copiers associated with reactive sizing agents. And finally, polymeric surface sizes added at the size press do not cause wet end deposit problems that can significantly reduce the productivity of the paper machine.

Sizing efficiency and cost are the most commonly cited disadvantages of polymeric surface sizing agents. On a pound-for-pound basis, AKD, AlkKD and ASA are 30% less expensive than a typical polymeric surface size. The high sizing efficiency of AKD, AlkKD, and ASA further increases the relative cost of obtaining sizing with polymeric surface sizes. All three reactive sizing agents are 50–100% more efficient than any commercial polymeric surface sizing agent on a pound-for pound basis.

Pilot paper machine testing has shown that liquid ketene multimer added at the size press offers a better balance of sizing efficiency, paper machine cleanliness, paper ink jet print quality, and paper runnability on high speed converting equipment than AKD, AlkKD, or ASA added at the wet end, or any polymeric surface sizing agent. Ketene multimer sizing agents have also shown advantages in paper grades, such as liquid packaging board, where wet strength is required.

Ketene multimer sizing agents based on aliphatic and alicyclic dicarboxylic acids are described in U.S. Pat. No. 5,685,815 and WO97/30218 and Brungardt, Riehle and Zhang 1, U.S. Ser. No. 08/601,113, filed Feb. 16, 1996, the entire disclosure of which references are incorporated by reference herein.

SUMMARY OF THE INVENTION

According to the present invention there is provided a sizing agent comprising a nucleophilic group (such as alcohol) terminated 2-oxetanone multimer.

Further provided is a process for preparing the nucleophic group terminated ketene multimer of the present invention comprising (a) providing a compound having at least one nucleophilic group (b) reacting said compound with a molar excess of dicarboxylic acid chloride in the presence of a base, e.g., triethylamine and optionally (c) removing the triethylamine hydrochloride salt byproduct of the reaction.

Still further provided according to the present invention is a method of sizing paper comprising sizing paper with the nucleophilic group terminated 2-oxetanone multimer of the present invention and paper sized with such surface sizing agent.

DETAILED DESCRIPTION OF THE INVENTION

A new class of sizing agent was made by reacting a compound having a nucleophilic group, such as an alcohol with a molar excess of a dicarboxylic acid chloride in the presence of a base that is suitable to catalyze the formation of ketene monomer and ketene dimer from carboxylic acid chlorides. Practically any tertiary amine is suitable, e.g. triethylamine, tripropylamine, tributylamine, dimethylaniline, etc. The preferred catalysts are the tertiary amines and the most preferred catalyst is triethyl amine.

Tertiary amines disclosed in U.S. Pat. No. 5,502,218 are suitable for use in the present invention. Accordingly the tertiary amine used in the present process can be a monoamine or diamine. The tertiary amine should be liquid at the reaction conditions. The tertiary amine is suitably a monoamine of the formula $R_1R_2R_3N$, wherein $R_1$, $R_2$ and $R_3$ independent of each other can be alkyl, alkenyl, aralkyl such as benzyl, or cycloalkyl groups having from 1 to 10 carbon atoms, or $R_1$ and $R_2$ together can form an alkylene chain having up to 6, preferably 4 to 5 carbon atoms, whereby the amines are selected so that the total number of carbon atoms give an amine which is liquid at the reaction conditions. Aliphatic amines are preferred and they preferably have from 1 to 6 carbon atoms in each R group. Suitable amines can be selected from triethylamine, diethylmethylamine, dimethylcyclohexylamine, di-isopropylethylamine, tripropylamine, N-methylpyrrolidine and N-methylpiperidine. The use of blends of two or more amines is, of course, also within the scope of the invention. Triethylamine (TEA) is the preferred tertiary amine, mainly for its physical properties and for economic reasons.

Although a monofunctional carboxylic acid chloride, such as those described in WO97/3018, can be incorporated into the reaction, it is not needed to control the molecular weight of the ketene multimer. Since no monofunctional carboxylic acid is needed, no low molecular weight ketene dimer that can interfere with paper performance on high speed converting equipment or toner adhesion is formed by the reaction.

Molecules containing any nucleophilic group, such as alcohols, carboxylic, acids, thiols, amines or phenols can be reacted with the dicarboxylic acid chloride. The flexibility of the reaction, and the types of functional groups that can be used, should make it possible to incorporate functional chemicals into the multimer backbone such as optical brighteners or biocides.

In principle, any 1°, 2°, or 3° alcohol that can be reacted to form a stable ester group can be used to make the alcohol terminated ketene multimer. In paper sizing applications, long chain saturated, unsaturated, or branched aliphatic alcohols such as 1-octanol, 1-decanol, 1-dodecanol, 1-tetradecanol, 1-hexadecanol, 1-octadecanol, and the corresponding branched or unsaturated alcohols, such as 1-hexadecenol, or 1-octadecenol (e.g., oleyl alcohol) are effective. Corresponding carboxylic acids, thiols and amines should also be effective. More specifically, alcohols containing 1–40 carbon atoms can be used. Alcohols containing 8–22 carbon atoms are more preferred. Alcohols containing 14–18 carbons atoms are most preferred. Functional groups that can be incorporated into the ketene multimer as part of the alcohol include: esters, ethers, tertiary and quaternary amines, carbon-to-carbon double and triple bonds, ketones, aldehydes, aliphatic rings, and aromatic rings. Di-, tri- or multifunctional alcohols can also be incorporated into the reaction.

The dicarboxylic acid moiety of the dicaboxylic acid chloride is selected from the group consisting of saturated and unsaturated dicarboxylic acids having from 4 to 44 carbon atoms including dimer acids having from 28 to 44 carbon atoms. The dimer acids can be saturated or unsaturated. Any of the dicarboxylic acids commonly used to make commercial polyesters and polyamides, and polyester oligomers, can be used to make the dicarboxylic acid chloride component of the reaction, including: succinic, adipic, suberic, azelaic, sebacic, dodecanedicarboxylic acid, and $C_{36}$ dimer acids such as Unidyme-14 available from Union Camp Chemical. Dicarboxylic acids containing from 8–12 carbon atoms are preferred, as are dicarboxylic acids formed by the dimerization of unsaturated fatty acids having from 32 to 36 carbon atoms (e.g., Unidyme-14). Small amounts of tri- and tetra- carboxylic acids can also be incorporated into the reaction to form branched or cross-linked alcohol terminated ketene multimers. Preferred dicarboxylic acids are sebacic, azelaic and dodecanedicarboxylic acid.

Although it is not needed to control the molecular weight of the alcohol terminated multimer, any mono-carboxylic acid chloride that contains the H atom next to the acid group needed for the formation of ketene monomer, and does not contain a functional group that interferes with the dimerization reaction, can be incorporated into the reaction. Mono-carboxylic acid chlorides made from carboxylic acids containing from 4 to 24 carbon atoms, such as, butanoic acid, pentanoic acid, hexanoic acid, heptanoic acid, octanoic acid, nonanoic acid, decanoic acid, dodecanoic acid, tetradecanoic acid, hexadecanoic acid, octadecanoic acid, and behenic acid can be used. The corresponding unsaturated and branched carboxylic acids can also be used. These acids include, but are not limited to: isostearic acid, oleic acid (octadecenoic acid), linoleic acid, and mixtures of oleic and linoleic acids such as Pamolyn 100, Pamolyn 200, Pamak-1, Pamak-131, or Pamolyn 380 fatty acids (available from Hercules Incorporated). Other unsaturated fatty acids that can be used include: dodecenoic, tetradecenoic (myristoleic), hexadecenoic (palmitoleic), octadecadienoic (linolelaidic), octadecatrienoic (linolenic), eicosenoic (gadoleic), eicosatetraenoic (arachidonic), docosenoic (erucic), docosenoic (brassidic), and docosapentaenoic (clupanodonic) acids.

The molecular weight of a nucleophilic group, such as alcohol terminated ketene multimer is determined, in part, by the molar ratio of dicarboxylic acid chloride to alcohol. As the mole ratio of dicarboxylic acid chloride to alcohol (alcohol plus mono-carboxylic acid if one is used) increases, the molecular weight of the resulting multimer increases. Ratios of dicarboxylic acid chloride to alcohol that can be used range from 4:1 to 1:1. More preferably from 2:1 to 1:1.

The sizing agent of the present invention is herein interchangeably referred to as nucleophilic group terminated ketene multimer or nucleophilic group terminated 2-oxetanone multimer.

The sizing agent of the present invention is preferably a nucleophilic group, preferably alcohol, terminated 2-oxetanone multimer having the formula (I).

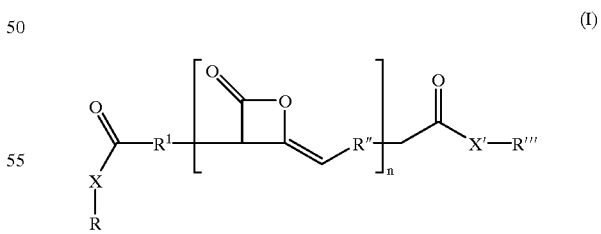

(I)

in which

R and R'" are independently linear, branched or cyclic hydrocarbons having from 1 to 40 carbon atoms which hydrocarbons optionally contain functional groups selected from the group consisting of esters, ethers, tertiary and quaternary amines, carbon-to-carbon double and triple bonds, ketones, aldehydes, aliphatic rings, and aromatic rings and di-, tri- and/or multifunctional alcohols, preferably having from 8 to 22 carbon atoms, and most preferably having from 14 to 18 carbon atoms;

R' is a linear, branched or alicyclic hydrocarbon having from 3 to 41 carbon atoms, preferably having from 5 to 9 carbon atoms, or if derived from dimer acids R' has from 25 to 41, preferably from 29 to 33 carbon atoms;

R" is a linear, branched or alicyclic hydrocarbon having from 2 to 40 carbon atoms, preferably having from 4 to 8 carbon atoms, or if derived from dimer acids R" has from 24 to 40, preferably from 28 to 32 carbon atoms;

X and X' are independently O, NH, S or COO; preferably O, and n is an integer from 1 to 10, preferably from 2 to 4.

The sizing agent of the present invention can be a mixture of 2-oxetanone multimers. When the sizing agent is such a mixture, preferably at least 25 weight percent of the mixture comprises multimers containing hydrocarbon substituents with irregularities, the hydrocarbon substituents with irregularities being selected from the group consisting of branched alkyl, linear alkenyl and branched alkenyl groups. Mixtures of the 2-oxetanone multimers preferably contain regio isomers of such multimer compounds and preferably contain an average n of from about 1 to about 10, and most preferably from 2 to 4.

These sizing agents may be prepared by known procedures; see, e.g., EP-A2-666,363, Brungardt, Riehle and Zhang 1, U.S. Ser. No. 08/601,113, filed Feb. 16, 1996 and WO97/30218, the disclosures of which are incorporated herein by reference. In the first step, an acid chloride is formed from a dicarboxylic acid, using phosphorous trichloride or another conventional chlorination agent. The acid chloride is then dehydrochlorinated in the presence of triethylamine or another suitable base, and a nucleophilic group containing compound, such as an alcohol, to form the 2-oxetanone multimer mixture. Stable emulsions of these surface sizing agents can be prepared in the same way as standard AKD emulsions.

The reaction of the nucleophilic group containing compounds, such as alcohol, with the dicarboxylic acid chloride can be carried out in the presence of triethylamine generally in an amount of from at least about a molar equivalence, preferably at least about 2% molar excess based on acid chloride. The triethylamine can be present in an amount up to about 50% molar excess, preferably up to about 6% molar excess based on acid chloride.

The reaction is generally carried out at a temperature of at least about 0° C., preferably at least about 40° C. The temperature can be up to about 100° C., preferably up to about 65° C.

Preferred chlorination and dimerization methods are described in Examples 1–3. Stable emulsions of alcohol terminated ketene multimers can be made using the method described in Example 4.

Nucleophilic group, such as alcohol terminated ketene multimers made by this method should be useful in papermaking applications that require sizing and/or wet strength. In sizing applications, addition levels of alcohol terminated ketene multimer ranging from 0.005–0.5% are preferred. Addition levels ranging from 0.05%–0.25% are more preferred. They are particularly suitable as surface sizing agents for paper. In wet strength applications, addition levels from 0.1–2.0% are preferred. Addition levels from 0.25–1% are more preferred. Since it should be possible to tailor alcohol terminated ketene multimers that give wet strength without significantly increasing sizing, they are also effective softening agents in paper tissue applications. Their unique chemical reactivity, and the ability to tailor hydrophobicity, also makes them useful in coupling agent, sealant, and adhesive applications.

The following examples are given for the purpose of illustration only and are not intended to limit the scope of the present invention. All parts and percentages are by weight unless otherwise indicated.

EXPERIMENTAL PROCEDURES

Paper for evaluation on the IBM 3800 was prepared on the pilot paper machine at Western Michigan University.

To make a typical forms bond papermaking stock, the pulp furnish (three parts Southern hardwood kraft pulp and one part southern softwood kraft pulp) was refined to 425 ml Canadian Standard Freeness (C.S.F.) using a double disk refiner. Prior to the addition of the filler to the pulp furnish (10% medium particle-size precipitated calcium carbonate), the pH (7.8–8.0), alkalinity (150–200 p.p.m.), and hardness (100 p.p.m.) of the papermaking stock were adjusted using the appropriate amounts of $NaHCO_3$ NaOH, and $CaCl_2$.

A 35-minute roll of paper from each paper making condition was collected and converted on a commercial forms press to two boxes of standard 8½"×11" forms. Samples were also collected before and after each 35 minute roll for natural aged size testing, basis weight (56 #/3000 $ft^2$), and smoothness testing.

The converted paper was allowed to equilibrate in the printer room for at least one day prior to evaluation. Each box of paper allowed a 10–14 minute (220 f.p.m.) evaluation on the IBM 3800. All samples were tested in duplicate. A standard acid fine paper was run for at least two minutes between each evaluation to reestablish initial machine conditions The height of billowing in inches at the end of the run, was used to measure the effectiveness of each approach.

The Hercules Size Test (HST) is a standard test in the industry for measuring the degree of sizing. This method employs an aqueous dye solution as the penetrant to permit optical detection of the liquid front as it moves through the sheet. The apparatus determines the time required for the reflectance of the sheet surface not in contact with the penetrant to drop to a predetermined percentage of its original reflectance. All HST testing data reported measured the seconds to 80% reflection with 1% formic acid ink mixed with naphthol green B dye (Hercules Test Ink #2) unless otherwise noted. The use of this formic acid ink is a more severe test than neutral ink and tends to give faster test times. High HST values are better than low values. The amount of sizing desired depends upon the kind of paper being made and the system used to make it.

EXAMPLE 1

Preparation of an Alcohol Terminated Ketene Multimer using Sebacic Acid Chloride and Oleyl Alcohol A reaction apparatus consisting of a 2-L jacketed kettle, two addition funnels, a condenser, and an overhead stirrer was oven dried (105° C.), then assembled while still hot under a nitrogen sparge. Once the reactor had cooled, the nitrogen sparge was stopped and the reactor was placed under a nitrogen blanket. 684 g of 1,2 dichloropropane (PDC) and 156.6 g of triethylamine were then added to the reactor. The overhead stirrer was started and the reactor was heated to 40° C. by recirculating hot water through the reactor jacket. 180 g of sebacic acid chloride (Aldrich Chemical Co., Inc.) and 101 g of oleyl alcohol (Aldrich Chemical Co., Inc.) were then separately added to the reactor over a 40 minute period. Cold water in the reactor jacket was used to maintain the temperature of the reaction mixture between 45 and 50° C. during the addition. Triethylamine hydrochloride salt, a by-product of the reaction, precipitated throughout the sebacic acid chloride/oleyl alcohol addition. Once the addition was complete, the temperature of the reaction mixture was maintained at 40° C. for 20 minutes by recirculating hot water in the reactor jacket. An I.R. spectrum of the mixture was then taken to determine if the desired reaction was complete. The reaction is considered to be complete if no residual acid chloride peak at 1800 $cm^{-1}$ is observed. Ketene dimer ring absorbances at 1870 $cm^{-1}$ and 1725 $cm^{-1}$ confirmed the presence of the desired ketene multimer. The larger than normal size of the absorbance at 1725 $cm^{-1}$ confirmed the presence of the desired ester formed by the reaction of ketene monomer with oleyl alcohol. Once the reaction was found to be complete by I.R., the triethylamine hydrochloride salt by-product of the reaction was removed by filtration using a Buchner funnel. The PDC solvent was then removed from the product on a roto-vap (60° C., vacuum pump). 182 g of the desired alcohol terminated ketene multimer product were isolated.

EXAMPLE 2

Chlorination of Unidyme-14 $C_{36}$ Dimer Acid

A reaction apparatus consisting of a 1-L jacketed kettle, an addition funnel, a condenser, and overhead stirrer was oven-dried (105° C.), then assembled while still hot under a nitrogen sparge. The reactor was then heated to 100° with a heat gun and dried under a constant flow of nitrogen. Once the reactor had cooled, the nitrogen sparge was stopped and the reactor was placed under a nitrogen blanket vented through a NaOH scrubber.

400 g of Unidyme-14 $C_{36}$ dimer acid (available from Union Camp Chemical Co.) was then added to the reactor, and heated to 70° C. by recirculating hot mineral oil through the jacket of the reactor. 97 g of $PCl_3$ were then added to the reactor over a fine minute period. Once the addition of $PCl_3$ was complete, the reaction mixture was stirred for an additional 15 minutes. The stirrer was then turned off and the phosphorous acids formed by the reaction were allowed to settle to the bottom of the reactor. After 20 minutes of settling, the phosphorous acid layer was removed from the bottom of the reactor. The reaction was then held at 70° C. and allowed to settle for an additional three hours. Small amounts of phosphorous acid were removed each hour over this time period. Finally, the desired acid chloride product was decanted away from a sticky yellow precipitate that formed around the bottom of the reactor and the excess $PCl_3$ was removed from the reaction product on a roto-vap (two hours, 70° C., vacuum pump). 406 g of the desired acid chloride were isolated.

EXAMPLE 3

Preparation of an Alcohol Terminated Ketene Multimer using Unidyme-14 Acid Chloride and Oleyl Alcohol A reaction apparatus consisting of a 250 mL jacketed 3-necked-round-bottomed flask, two additional funnels, a condenser, and overhead stirrer was oven-dried (105° C.), then assembled while still hot under a nitrogen sparge. Once the reactor had cooled, the nitrogen sparge was stopped and the reactor was placed under a nitrogen blanket. 49.5 g of 1,2-dichloropropane (PDC) and 5.24 g of triethylamine were then added to the reactor. The overhead stirrer was started and the reactor was heated to 40° C. by recirculating hot water through the reactor jacket. 15.0 g of Unidyme-14 acid chloride made by the method described in Example 2 and 3.37 g of oleyl alcohol (Aldrich) were then separately added to the reactor over a 20 minute period. Cold water in the reactor jacket was used to maintain the temperature of the reaction mixture between 45 and 50° C. Triethylamine hydrochloride salt, a by-product of the reaction, precipitated throughout the acid chloride/oleyl alcohol addition. Once the addition was complete, the temperature of the reaction mixture was maintained at 40° C. for 20 minutes by recirculating hot water in the reactor jacket. An I.R. spectrum of the mixture was then taken to determine if the desired reaction was complete. The reaction is considered to be complete if no residual acid chloride peak at 1800 $cm^{-1}$ is observed. Ketene dimer ring absorbance at 1870 $cm^{-1}$ and 1725 $cm^{-1}$ confirmed the presence of the desired ketene multimer. The larger than normal size of the absorbance at 1725 $cm^{-1}$ confirmed the presence of the desired ester formed by the reaction of ketene monomer with oleyl alcohol. Once the reaction was found to be complete by I.R., the triethylamine hydrochloride salt by-product of the reaction was removed by filtration using a Buchner funnel. The PDC solvent was then removed from the product on a roto-vap (60° C., vacuum pump). 7.5 g of the desired alcohol terminated ketene multimer product was isolated.

EXAMPLE 4

Preparation of Aqueous Emulsions of Alcohol Terminated Ketene Multimers

The 2-oxetanone sizing agent emulsions, including the multimer emulsions, were prepared according to the disclosure of U.S. Pat. No. 4,317,756, which is incorporated herein by reference, with particular reference to Example 5 of the patent.

A sizing agent emulsion of a ketene multimer (or dimer) may be prepared by admixing 880 parts of water, 60 parts of cationic corn starch and 10 parts of sodium lignin sulfonate. The mixture is adjusted to pH of about 3.5 with sulfuric acid. The resulting mixture is heated at 90°–95° C. for about one hour. Water is then added to the mixture in an amount sufficient to provide a mixture of 1750 parts (total weight). About 240 parts of the ketene multimer (or dimer) is stirred into the mixture together with 2.4 parts of thiadiazine preservative. The resulting premix (at 65° C.) is homogenized in one pass through an homogenizer at 3000 p.s.i. The homogenized product is diluted with water to a ketene multimer (or dimer) solids content within the range of about 6% to about 30% to form a sizing agent emulsion; it should be understood that the precise solids content of the sizing agent emulsion is not critical.

EXAMPLES 5 TO 10 AND COMPARATIVE EXAMPLES 1 to 3

Evaluation of Sizing Efficiency

The sizing efficiencies of the alcohol terminated multimer emulsions described in Example 4 were evaluated by adding them, along with size press starch, to an unsized base sheet using a laboratory puddle size press (4% starch pickup, GPC D-150 oxidized starch, available from Grain Processing Co.). The composition of the base sheet is listed below.

70% of Hardwood kraft

30% of Softwood kraft

15% of Albacar HO (available from Specialty Mineral Inc.)

0.75% of Sta-Lok 400 cationic starch (available from A. E. Saley Co.)

0.2% of Alum

The amount of sizing agent added with the size press starch was adjusted by varying the concentration of the sizing emulsion in the size press starch solution. A standard ketene multimer made from a 2:1 molar mixture of sebacic acid and Pamak-131 fatty acid (available from Hercules Incorporated) was evaluated as a control. The standard ketene multimer used as control was prepared following the procedure of Example 1 of WO97/30218A filed on Feb. 16, 1996, the disclosure of which application has already been incorporated above by reference, herein with particular reference to Example 1 of the application. Accordingly the chlorination of the fatty acid and dicarboxylic acid mixture was carried out in a 500 mL glass-jacketed reactor fitted with a condenser, an addition funnel, and nitrogen adapters, which was sparged with nitrogen gas (each piece of glassware having been oven dried at 105° C. prior to assembly). The nitrogen gas flow was vented through a NaOH scrubber. The reactor was initially heated to 105° C. with a heat gun and cooled under a steady stream of nitrogen.

The dehydrochlorination of the acid chloride reaction product was carried out in a 1 L glass-jacketed reactor fitted with a condenser, an addition funnel, and nitrogen adapters, was sparged with nitrogen gas (each piece of glassware having been oven dried at 105° C. prior to assembly). The reactor was initially heated to 105° C. with a heat gun and cooled under a steady stream of nitrogen.

The addition levels that were used and the results of HST testing of the resulting paper are given below.

EXAMPLE 11–12 AND COMPARATIVE EXAMPLES 4 to 7

Evaluation of IBM 3800 Paper

Paper for IBM 3800 runnability testing was made on the pilot paper machine at Western Michigan University (WMU). A typical forms bond papermaking furnish was used. The pulp (three parts hardwood kraft pulp and one part softwood kraft pulp) was refined to 425 mL Canadian Standard Freeness (C.S.F.) using a double disk refiner. Prior to the addition of the filler to the pulp (10% Albacar 5970 medium particle-size precipitated calcium carbonate, available from Specialty Minerals Inc.), the pH (7.5–8.0), alkalinity (150–200 p.p.m.), and hardness (100 p.p.m.) of the papermaking stock were adjusted using the appropriate amounts of $NaHCO_3$, NaOH, and $CaCl_2$.

To simulate a standard forms papermaking furnish, wet-end additions of internal sizing agent ($2^{nd}$ mix box, Precis® 2000 sizing agent, available from Hercules, linoleic acid ketene dimer), quaternary-amine-substituted cationic starch ($1^{st}$ mix box overflow, Sta-Lock 400, available from A. E. Staley Co., 0.50%), and alum ($2^{nd}$ mix box overflow, 0.2%) were carried out. Stock temperature at the white water tray was controlled at 49° C. The wet presses were set at 207 centimeters of Hg. A dryer profile that gave 1–2% moisture a the size press and 4–6% moisture a the reel was used (0.39 meters/second paper machine speed). Approximately 40 kg/metric tonne of an oxidized cornstarch and 2.5 kg/metric tonne of NaCl were added at the size press (Grain Processing Co. D-15F oxidized corn starch, 55° C., pH 7.5–8.0). Calendar pressure and reel moisture were adjusted to obtain a Sheffield smoothness of 150 flow units t the reel (Column #2 felt side up).

As shown in Table 2, oleyl alcohol terminated ketene multimers based on sebacic acid and a $C_{36}$ dimer acid were evaluated. As described above, paper billowing height on an IBM 3800 high speed printer was used as a measure of paper runnability. This testing showed that both alcohol terminated ketene multimers gave good runnability. This testing

TABLE 1

| Example | Sizing Agent | Size Pick-Up | HST (Seconds) |
| --- | --- | --- | --- |
| C-1: | 1 sebacic acid:fatty acid feedstock[(1)]Ketene multimer | 0.075% | 5 |
| C-2: | 1 sebacic acid:fatty acid feedstock[(1)]ketene multimer | 0.125% | 413 |
| C-3: | 1 sebacic acid:fatty acid feedstock[(1)]ketene multimer | 0.175% | 410 |
| 5: | 1 sebacic acid:oleyl alcohol terminated ketene multimer | 0.075% | 1 |
| 6: | 1 sebacic acid:oleyl alcohol terminated ketene multimer | 0.125% | 211 |
| 7: | 1 sebacic acid:oleyl alcohol terminated ketene multimer | 0.175% | 225 |
| 8: | 1 Unidyme-14:oleyl alcohol terminated ketene multimer | 0.075% | 1 |
| 9: | 1 Unidyme-14:oleyl alcohol terminated ketene multimer | 0.125% | 98 |
| 10: | 1 Unidyme-14:oleyl alcohol terminated ketene multimer | 0.175% | 194 |

[(1)]Fatty acid feedstock comprising a 1:1 blend of oleic acid and linoleic acid.

These data show that alcohol terminated ketene multimers can give the 50–150 seconds of HST sizing needed for most fine paper applications at moderated addition levels (Ex. 6,7,9 and 10).

showed that both alcohol terminated ketene multimers gave good runnability (billowing height less than 3") at the addition levels needed to obtain the levels of sizing needed in most fine paper applications.

TABLE 2

| Example | Internal Size Ketene Dimer Made From Linoleic Acid | Surface Additive | S.P. Starch Add'n Level | Maximum Billow (felt/wire) |
|---|---|---|---|---|
| C-4 | 0.065% | 0.05% of Ketene dimer made from fatty acid feedstock[1] | 80–85 #/ton | 2.25/2.00 |
| C-5 | 0.065% | 0.10% of Ketene dimer made from fatty acid feedstock[1] | 80–85 #/ton | 2.12/2.00 |
| C-6 | 0.065% | 0.05% of C-I ketene multimer | 80–85 #/ton | 2.12/2.00 |
| C-7 | 0.065% | 0.10% of C-I ketene multimer | 80–85 #/ton | 2.12/1.87 |
| C-11 | 0.065% | 0.15% 2:1 sebacic acid:oleyl alcohol terminated ketene multimer | 80–85 #/ton | 2.12/1.87 |
| C-12 | 0.065% | 0.15% 2:1 Unidyme-14:oleyl alcohol terminated ketene multimer | 80–85 #/ton | 2.50/2.00 |

[1]Fatty acid feedstock comprising 1:1 blend of oleic acid and linoleic acid.

What is claimed is:

1. A process of preparing nucleophilic group terminated ketene multimers comprising:
   (a) providing a compound having at least one nucleophilic group,
   (b) reacting said compound with a molar excess of dicarboxylic acid chloride in the presence of a base catalyst and optionally,
   (c) removing the salt by product of the reaction.

2. The process of claim 1 wherein the base is tertiary amine.

3. The process of claim 2 wherein the compound having a nucleophilic group is selected from the group consisting of alcohols, carboxylic acids, thiols, amines and phenols.

4. The process of claim 2 wherein the compound having a nucleophilic group is selected from group consisting of primary-, second- and tertiary alcohols.

5. The process of claim 2 wherein the compound having a nucleophilic group is selected from the group consisting of saturated, unsaturated and branched aliphatic mono-, di-, tri- and multifunctional, alcohols having from 1 to 40 carbon atoms.

6. The process of claim 4 wherein the alcohol has at least one functional group selected from the group consisting of esters, ethers, tertiary and quaternary amines, carbon to carbon double and triple bonds, ketones, aldehydes, aliphatic rings and aromatic rings.

7. The process of claim 2 wherein the dicarboxylic acid moiety of the dicarboxylic acid chloride is selected from the group consisting of saturated and unsaturated, linear, branched and alicyclic dicarboxylic acids having from 4 to 44 carbon atoms.

8. The process of claim 2 wherein the dicarboxylic acid moiety of the dicarboxylic acid chloride is selected from the group consisting of dimer acids having from 28 to 44 carbon atoms.

9. The process of claim 1 wherein the dicarboxylic acid moiety of the dicarboxylic acid chloride is selected from the group consisting of succinic, adipic, suberic, sebacic, azelaic and dodecanedicarboxylic acid, and dimer acids having from 32 to 36 carbon atoms.

10. The process of claim 8 wherein carboxylic acid moieties selected from the group consisting of mono-, tri-, and tetra-carboxylic acid, alkenyl succinic anhydride and fluorinated alkyenyl succinic anhydride are incorporated in the dicarboxylic acid chloride.

11. The process of claim 10 wherein the carboxylic acid moieties are selected from the group consisting of saturated, unsaturated and branched mono-carboxylic acids.

12. The process of claim 11 wherein the carboxylic acid moieties are selected from the group consisting of butanoic acid, pentanoic acid, hexanoic acid, heptanoic acid, octanoic acid, decanoic acid, dodecanoic acid, tetradecanoic acid, hexadecanoic acid, octadecanoic acid, behenic acid, isostearic acid, oleic acid (octadecenoic acid), linoleic acid, mixtures of oleic acid and linoleic acids, dodecenoic acid, tetradecenoic (myristoleic) acid, hexadecenoic (palmitoleic) acid, octadecadienoic (linoledaidic) acid, octadecatrienoic (linolenic) acid, eicosenoic (gadoleic) acid, eicosatetraenoic (arachidonic) acid, docosenoic (erucid) acid, docosenoic (brassidic) acid, and docosapentaenoic (clupanodonic) acids.

13. The process of claim 2 wherein the molar ratio ratio of dicarboxylic acid chloride to the compound having at least one nucleophilic group is up to about 4:1.

14. The process of claim 2 wherein the amount of tertiary amine is at least about the molar equivalent of dicarboxylic acid chloride.

15. The process of claim 2 wherein the amount of tertiary amine is up to about 50% molar excess based on dicarboxylic acid chloride.

16. The process of claim 2 wherein the reaction is carried out at a temperature of at least 0° C.

17. The process of claim 1 wherein the reaction is carried out at a temperature of up to about 100° C.

18. The process of claim 2 wherein the nucleophilic group has at least one functional group selected from the group consisting of esters, ethers, tertiary and quaternary amines, carbon-to-carbon double and triple bonds, ketones, aldehydes, aliphatic rings, aromatic rings, and di-, tri- and multifunctional alcohols.

19. The process of claim 4 wherein the base is tertiary amine, the dicarboxylic acid moiety of the dicarboxylic acid is selected from the group consisting of saturated and unsaturated linear, branched and alicyclic dicarboxylic acids having from 4 to 44 carbon, and dimer acids having from 28 to 44 carbon atoms, the molar ration of dicarboxylic acid chloride to the compound having at least one nucleophilic group is up to about 4:1, the amount of tertiary amine is from about 0 to 50% molar excess based on dicarboxylic acid chloride, and the reaction is carried out at a temperature of from about 0 to about 100° C.

20. The process of claim 18 wherein the tertiary amine is triethylamine.

21. The process of claim 19 wherein the nucleophilic group is selected from the group consisting of saturated, unsaturated and branched aliphatic alcohols having from 8 to 22 carbon atoms.

22. The process of claim 21 wherein the alcohol is selected from the group consisting of 1-octanol, 1-decanol, 1-dodecanol, 1-tetradecanol, 1-hexadecanol, 1-octadecanol, 1-hexadecenol and 1-octadecenol.

23. The process of claim 19 wherein the dicarboxylic acid moiety of the dicarboxylic acid chloride is selected from the group consisting of saturated dicarboxylic acids having from 8 to 12 carbon atoms and unsaturated dimer acids having from 32 to 36 carbon atoms.

24. The process of claim 19 wherein the dicarboxylic acid moiety of the dicarboxylic acid chloride is selected from the group consisting of sebacic acid, azelaic acid, dodecanedicarboxylic acid and dimer acid having 36 carbon atoms.

25. The process of claim 19 wherein the molar ratio of dicarboxylic acid chloride to the compound having at least one nucleophilic group is up to about 2:1.

26. The process of claim 19 wherein the amount of tertiary amine is at least about 2% molar excess based on dicarboxylic acid chloride.

27. The process claim 19 wherein the amount of tertiary amine is up to about 6% molar excess based on dicarboxylic acid chloride.

28. The process of claim 19 wherein the reaction is carried out at a temperature of at least about 40° C.

29. The process of claim 19 wherein the reaction is carried out at a temperature of up to about 65° C.

30. The process of claim 21 wherein the tertiary amine is triethylamine, the dicarboxylic acid moiety of the dicarboxylic acid chloride is selected from the group consisting of saturated dicarboxylic acids having from 8 to 12 carbon atoms and unsaturated dimer acids having from 32 to 36 carbon atoms, the molar ratio of dicarboxylic acid chloride to the compound having at least one nucleophilic group is up to about 2:1, the amount of triethylamine is from about 2 to about 6% molar excess based on dicarboxylic acid chloride and the reaction is carried out at a temperature of from about 40 to about 65° C.

31. The process of claim 21 wherein the alcohol has from 14 to 18 carbon atoms.

32. The process of claim 30 wherein the alcohol has from 14 to 18 carbon atoms.

33. A sizing agent comprising a nucleophilic group terminated 2-oxetanone multimer.

34. The sizing agent of claim 33 comprising a mixture of nucleophilic group terminated 2-oxethanone multimers wherein at least 25 weight percent of the mixture comprises multimers containing hydrocarbon substituents with irregularities, the hydrocarbon substituents with irregularities being selected from the group consisting of branched alkyl, linear alkenyl and branched alkenyl groups.

35. The sizing agent of claim 33 wherein the nucleophilic group terminated 2-oxetanone multimer has the formula (I):

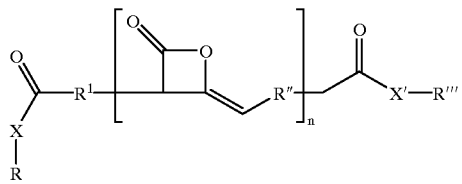

(I)

In which
R and R''' are independently linear, branched or cyclic hydrocarbons having from 1 to 40 carbon atoms, which hydrocarbons optionally contain functional groups selected from the group consisting of esters, ethers, tertiary and quaternary amines, carbon-to-carbon double and triple bonds, ketones, aldehydes, aliphatic rings, and aromatic rings and di-, tri- and/or multifunctional alcohols;

R' is a linear, branched or alicyclic hydrocarbon of from 3 to 41 carbon atoms, or if derived from dimer acids R' has from 25 to 41 carbon atoms;

R" is a linear, branched or alicyclic hydrocarbon having from 2 to 40 carbon atoms, or if derived from dimer acids, R" has from 24 to 40 carbon atoms;

X and X' are independently O, NH, S, or COO; and n is an integer from 1 to 10.

36. The sizing agent of claim 34 wherein the nucleophilic group terminated 2-oxetanone multimers have the formula (I).

37. The sizing agent of claim 33 wherein the nucleophilic group is selected from the group consisting of alcohols, carboxylic acids, thiols, amines and phenols.

38. The sizing agent of claim 33 wherein the nucleophilic group is selected from the group consisting of primary- secondary- and tertiary alcohols.

39. The sizing agent of claim 33 wherein the nucleophilic group is selected from the group consisting of saturated, unsaturated and branched aliphatic mono-, di-, tri- and multifunctional alcohols having from 1 to 40 carbon atoms.

40. The sizing agent of claim 38 wherein the alcohol has at least one functional group selected from the group consisting of esters, ethers, tertiary and quaternary amines, carbon to carbon double and triple bonds, ketenes, aldehydes, aliphatic rings and aromatic rings.

41. The sizing agent of claim 35 wherein the hydrocarbon portions R' and R" are derived from saturated and unsaturated linear, branched and alicyclic dicarboxylic acids having from 4 to 44 carbon atoms and dimer acids having 28 to 44 carbon atoms.

42. The sizing agent of claim 35 wherein the hydrocarbon portions R' and R" are derived from dimer acids having from 28 to 44 carbon atoms.

43. The sizing agent of claim 35 wherein the hydrocarbon portions R' and R" are derived from succinic, adipic, suberic, azelaic, sebacic and dodecanedicarboxylic acids and dimer acids, having from 32 to 36 carbon atoms.

44. The sizing agent of claim 41 wherein a portion of the dicarboxylic acids are substituted with mono-, tri-, and/or tetra-carboxylic acids, alkenyl succinic anhydride and/or fluorinated alkenyl succinic anhydride.

45. The sizing agent of claim 44 wherein a portion of the dicarboxylic acids are substituted with saturated, unsaturated and/or branched mono-carboxylic acids.

46. The sizing agent of claim 45 wherein the mono-carboxylic acid is selected from the group consisting of butanoic acid, pentanoic acid, hexanoic acid, heptanoic acid, octanoic acid, nonanoic acid, decanoic acid, dodecanoic acid, tetradecanoic acid, hexadecanoic acid, octadecanoic acid, behenic acid, isostearic acid, oleic acid (octadecenoic acid), linoleic acid, mixtures of oleic and linoleic acids, dodecenoic acid, tetradecenoic (myristoleic) acid, hexadecenoic (palmitoleic) acid, octadecadienoic (linolelalidic) acid, octadecatrienoic (linolenic) acid, eicosenoic (gadoleic) acid, eicosatettraenoic (arachiodonic) acid, docosenoic (erucic) acid, docosenoic (brassidic) acid, and docosapentaenoic (clupanodonic) acid.

47. The sizing agent of claim 35 wherein
R and R''' are independently hydrocarbons having from 8 to 22 carbon atoms;
R' is a hydrocarbon having from 5 to 9 carbon atoms when derived from monomeric dicarboxylic acids and from 25 to 41 carbon atoms when derived from dimer acids;
R" is a hydrocarbon having from 4 to 8 carbon atoms when derived from monomeric dicarboxylic acids and from 24 to 40 carbon atoms when derived from dimer acids;
X and X' are O and
n is an integer from 2 to 4.

48. The sizing agent of claim 35 wherein the hydrocarbon portions R' and R" are derived from saturated and unsaturated dicarboxylic acids having from 4 to 18 carbon atoms, and dimer acids having from 28 to 44 carbon atoms.

49. The sizing agent of claim 48 wherein the nucleophilic group is selected from the group consisting of saturated, unsaturated and branched aliphatic alcohols having from 8 to 22 carbon atoms.

50. The sizing agent of claim 35 wherein the hydrocarbon portion of R' and R" are derived from dicaboxylic acids having from 8 to 12 carbon atoms and unsaturated dimer acids having from 32 to 36 carbon atoms.

51. The sizing agent of claim 48 wherein the hydrocarbon portion R' and R" are derived from dicarboxylic acids selected from the group consisting of sebacic acid, azelaic acid, dodecanedicarboxylic acid and dimer acid having 36 carbon atoms.

52. The sizing agent of claim 48 wherein R and R'" are independently hydrocarbons having from 10 to 18 carbon atoms.

53. The sizing agent of claim 49 wherein the hydrocarbon portion of R' and R" are derived from dicarboxylic acids having from 8 to 12 carbon atoms and unsaturated dimer acids having from 32 to 36 carbon atoms and R and R'" are independently hydrocarbons having from 10 to 18 carbon atoms.

54. The sizing agent of claim 49 wherein the alcohol has from 14 to 18 carbon atoms.

55. A method of sizing paper comprising sizing paper with the nucleophilic group terminated 2-oxetanone multimer of claim 33.

56. A method of sizing paper comprising sizing paper with the nucleophilic group terminated 2-oxetanone multimer of claim 39.

57. A method of sizing paper comprising sizing paper with the nucleophilic group terminated 2-oxetanone multimer of claim 41.

58. A method of sizing paper comprising sizing paper with the nucleophilic group terminated 2-oxetanone multimer of claim 44.

59. A method of sizing paper comprising sizing paper with the nucleophilic group terminated 2-oxetanone multimer of claim 48.

60. A method of sizing paper comprising sizing paper with the nucleophilic group terminated 2-oxetanone multimer of claim 49.

61. A method of sizing paper comprising sizing paper with the nucleophilic group terminated 2-oxetanone multimer of claim 50.

62. A method of sizing paper comprising sizing paper with the nucleophilic group terminated 2-oxetanone multimer of claim 53.

63. Paper sized with the nucleophilic group terminated 2-oxetanone multimer of claim 33.

64. Paper sized with the nucleophilic group terminated 2-oxetanone multimer of claim 56.

65. Paper sized with the nucleophilic group terminated 2-oxetanone multimer of claim 57.

66. Paper sized with the nucleophilic group terminated 2-oxetanone multimer of claim 58.

67. Paper sized with the nucleophilic group terminated 2-oxetanone multimer of claim 59.

68. Paper sized with the nucleophilic group terminated 2-oxetanone multimer of claim 60.

69. Paper sized with the nucleophilic group terminated 2-oxetanone multimer of claim 61.

70. Paper sized with the nucleophilic group terminated 2-oxetanone multimer of claim 62.

71. A sizing agent comprising the sizing agent of claim 33 and at least one other sizing agent selected from the group consisting of alkenyl succinic anhydride, alkyl ketene dimer and alkenyl ketene dimer.

72. The sizing agent of claim 71 comprising at least 25% by weight of nucleophlilic group terminated 2-oxetanone multimer.

73. A sizing agent comprising the sizing agent of claim 35 and at least one other sizing agent selected from the group consisting of alkenyl succinic anhydride, alkyl ketene dimer and alkenyl ketene dimer.

74. The sizing agent of claim 73 comprising at least 25% by weight of nucleophilic group terminated 2-oxetanone multimer.

75. A method of sizing paper comprising surface sizing paper with the nucleophilic group terminated 2-oxetanone multimer of claim 33.

76. A method of sizing paper comprising surface sizing paper with the sizing agent of claim 71.

77. Paper surface sized with the nucleophilic group terminated 2-oxetanone multimer of claim 33.

78. Paper surface sized with the sizing agent of claim 71.

\* \* \* \* \*